US011642352B2

(12) United States Patent
MacAllister et al.

(10) Patent No.: US 11,642,352 B2
(45) Date of Patent: *May 9, 2023

(54) METHODS OF TREATING WANDERING IN LEWY DODY DEMENTIA

(71) Applicant: WOOLSEY PHARMACEUTICALS, INC., New York, NY (US)

(72) Inventors: Thomas MacAllister, Arlington, VA (US); Sven Jacobson, New York, NY (US)

(73) Assignee: Woolsey Pharmaceuticals, Inc., St. Petersburg, FL (US)

( * ) Notice: Subject to any disclaimer, the term of this patent is extended or adjusted under 35 U.S.C. 154(b) by 154 days.

This patent is subject to a terminal disclaimer.

(21) Appl. No.: 17/144,802

(22) Filed: Jan. 8, 2021

(65) Prior Publication Data

US 2021/0299140 A1  Sep. 30, 2021

Related U.S. Application Data

(60) Provisional application No. 63/005,913, filed on Apr. 6, 2020, provisional application No. 62/994,527, filed on Mar. 25, 2020.

(51) Int. Cl.
*A61K 31/551* (2006.01)
*A61P 25/28* (2006.01)

(52) U.S. Cl.
CPC ............ *A61K 31/551* (2013.01); *A61P 25/28* (2018.01)

(58) Field of Classification Search
CPC combination set(s) only.
See application file for complete search history.

(56) References Cited

U.S. PATENT DOCUMENTS 7,125,567 B2 * 10/2006 Sugi .................... A61K 31/551
424/497
2009/0318485 A1  12/2009 Borchardt et al.

FOREIGN PATENT DOCUMENTS

| JP | 6-293643 A | 10/1994 |
|---|---|---|
| WO | 2005117896 A1 | 12/2005 |
| WO | 2008/019395 A2 | 2/2008 |
| WO | 2008/021210 A2 | 2/2008 |
| WO | 2009/151845 A1 | 12/2009 |
| WO | 2009155777 A1 | 12/2009 |
| WO | 2013135596 A1 | 9/2013 |
| WO | 2017/195224 A1 | 11/2017 |

OTHER PUBLICATIONS

Kim (Alpha-synuclein biology in Lewy body diseases, Alzheimer's Research & Therapy 2014, 6:73).*
Cipriani (Wandering and dementia, Psychogeriatric, 2014, 14, 135-142).*
Algase, et al., "The Algase wandering scale: Initial psychometrics of a new caregiver reporting tool," Am J Alzheimers Dis Other Demen., (2001), vol. 16, No. 3: 141-152.
Algase, et al., "Impact of Cognitive Impairment on Wandering Behavior," West J Nurs Res., (2001), vol. 23, No. 3:283-95.
Aud, Myra A., "Dangerous wandering: Elopements of older adults with dementia from long-term care facilities," Am J Alzheimers Dis Other Demen., (2004), vol. 19, No. 6: 361-368.
Ballard, et al., "Wandering in Dementia Sufferers," Int J Geriatr Psych, (1991), vol. 6: 611-614.
Bathgate, et al., "Behaviour in frontotemporal dementia, Alzheimer's disease and vascular dementia," Acta Neurol Scand., (2001), vol. 103: 367-378.
Ceyzeriat, et al., "Learning from the Past: A Review of Clinical Trials Targeting Amyloid, Tau and Neuroinflammation in Alzheimer's Disease," Current Alzheimer Research, (2020), vol. 17: 1-13.
Chen, et al., "Fasudil and its analogs: A new powerful weapon in the long war against central nervous system disorders?" Expert Opin Investig. Drugs., (2013), vol. 22, No. 4: 537-50.
Cipriani, et al., "Wandering and dementia," Psychogeriatrics, (2014), vol. 14: 135-42.
Cooper, et al. "Risk Factor and Behavioral Differences Between Vascular and Alzheimer's Dementias: The Pathway to End-Stage Disease," J Geriatr Psychiatry Neurol., (1993), vol. 6: 29-33.
Couch, et al., "Increased Dendrite Branching in AβPP/PS1 Mice and Elongation of Dendrite Arbors by Fasudil Administration," Alzheimers Dis., (2010), vol. 20, No. 4: 1003-1008.
Erkinjuntti, et al., "Limitations of Clinical Criteria for the Diagnosis of Vascular Dementia in Clinical Trials. Is a Focus on Subcortical Vascular Dementia a Solution?," Ann N Y Acad Sci., (2000), vol. 903: 262-72.
Feng, et al., "Rho Kinase (ROCK) Inhibitors and Their Therapeutic Potential," J Med Chem., (2016), vol. 59: 2269-2300.
Folstein, et al. "'Mini-mental state': a practical method for grading the cognitive state of patients for the clinician," J Psychiatr Res., (1975), vol. 12: 189-198.
Hamano, et al., "Rho-kinase ROCK inhibitors reduce oligomeric tau protein," Neurobiology of Aging, (2020), vol. 89: 41-54.
Hou, et al., "Changes in hippocampal synapses and learning-memory abilities in a streptozotocin-treated rat model and intervention by using fasudil hydrochloride," Neuroscience, (2012), vol. 200: 120-129.
Human Rights Watch. 2018. They Want Docile: How Nursing Homes in the United StatesOvermedicate People with Dementia. ISBN: 978-1-623-135720. Downloaded May 17, 2019from http://www.hrw.org.

(Continued)

*Primary Examiner* — Kathrien A Hartsfield
(74) *Attorney, Agent, or Firm* — McBee Moore & Vanik IP, LLC; Susan McBee

(57) ABSTRACT

The invention is based on the discovery that rho kinase inhibitors can be used to treat proteinopathy associated wandering. A number of degenerative neurological diseases are thought to be caused, at least in part, by the formation of protein aggregates that cause neurotoxicity and progressive decline in function. The inventive methods related to the use of rho kinase inhibitors in the treatment of patients with proteinopathy-associated wandering. The patients may be suffering from Huntington's disease, a traumatic brain injury, autism spectrum disorder, Down syndrome or a proteinopathy-associated dementia, such as Alzheimer disease or frontotemporal dementia.

12 Claims, No Drawings

(56) References Cited

OTHER PUBLICATIONS

Jacobs, et al., "The structure of dimeric ROCK I reveals the mechanism for ligand selectivity," J Biol Chem., (2006), vol. 281(1): 260-68.
Kamei, et al., "Evaluation of Fasudil Hydrochloride Treatment for Wandering Symptoms in Cerebrovascular Dementia with 31P-Magnetic Resonance Spectroscopy and Xe-Computed Tomography," Clin Neuropharmacol., (1996), vol. 19, No. 5: 428-38.
Kamei, et al., "Effect of fasudil hydrochloride on wandering symptoms of cerebrovascular dementia patients," Neurotherapy, (1996), vol. 13: 43-50.
Kim, et al., Diagnostic Accuracy of Mini-Mental Status Examination and Revised Hasegawa Dementia Scale for Alzheimer's Disease, Dement Geriatr Cogn Disord., (2005), vol. 19: 324-30.
Klein, et al., "Wandering behaviour in community-residing persons with dementia," Intl J Geriatric Psychiatry, (1999), vol. 14: 272-279.
Knuffman, et al., "Differentiating Between Lewy Body Dementia and Alzheimer's Disease: A Retrospective Brain Bank Study," J Am Med Dir Assoc., (2001), vol. 2: 146-8.
Lai, et al., "Wandering behaviour in people with dementia," J Adv Nurs., (2003), vol. 44(2): 173-182.
Logsdon, et al., "Wandering: A Significant Problem Among Community-Residing Individuals with Alzheimer's Disease," The Journals of Gerontology Series B Psychological Sciences and Social Sciences, (1998), vol. 53B, No. 5: p. 294-9.
Nakagawa, et al., "ROCK-I and ROCK-II, two isoforms of Rho-associated coiled-coil forming protein serine/threonine kinase in mice," FEBS Lett., (1996), vol. 392: 189-93.
Roman, et al., "Vascular dementia: Diagnostic criteria for research studies, Report of the NINDS-AIREN International Workshop," Neurology, (1993), vol. 43: 250-60.
Salardini, Arash, "An Overview of Primary Dementias as Clinicopathological Entities," Semin Neurol., (2019), vol. 39: 153-166.
Sasaguri, et al., "APP mouse models for Alzheimer's disease preclinical studies," EMBO J., (2017), vol. 36, No. 17: 2473-2487.
Sellers, et al., "Amyloid β synaptotoxicity is Wnt-PCP dependent and blocked by fasudil," Alzeimer's & Dementia, (2018), vol. 14: 306-317.
Shibuya, et al., "Effect of Fasudil HCl, a Protein Kinase Inhibitor, on Cerebral Vasospasm," Acta Neurochir Suppl., (2001), vol. 77: 201-4.
Turk, Mari, "The Effect of Rho Kinase Inhibitors on Alzheimer's Disease," Dissertation, Arizona State University, May 2017.
Uehata, et al., "Calcium sensitization of smooth muscle mediated by a Rho-associated protein kinase in hypertension," Nature, (1997), vol. 389: 990-4.
Yamaguchi, et al., "Structural Basis for Induced-Fit Binding of Rho-Kinase to the Inhibitor Y-27632," J Biochem., (2006), vol. 140: 305-11.
Yayama, et al., "Discrepancy between subjective and objective assessments of wandering behaviours in dementia as measured by the Algase Wandering Scale and the Integrated Circuit tag monitoring system," Psychogeriatrics, (2013), vol. 13: 80-87.
Yu, et al., "Fasudil improves cognition of APP/PS1 transgenic mice via inhibiting the activation of microglia and shifting microglia phenotypes from M1 to M2," Chin J Cell Mol Immunol., (2017), vol. 33(12): 1585-1593.
Wick, et al., "Aimless Excursions: Wandering in the Elderly," Consult Pharm, (2006), vol. 21, No. 8: 608-618.
Elliott, et al., "A role for APP in Wnt signalling links synapse loss with β-amyloid production," Translational Psychiatry, (2018), vol. 8: 179.
Nelson, et al., (Eds), "Evidence-based Protocols for Wandering Behaviour," (2007), Springer Publishing Company, New York, NY.
Nakaoka, et al., "Pacing and Lapping Movements Among Institutionalized Patients With Dementia," Am J Alzheimers Dis Other Demen, (2010), vol. 25: 167-72.
Rovner, et al., "Mini-Mental State Exam in Clinical Practice," Hosp Pract., (1987), vol. 22(1A): 99, 103, 106, 110.
Becker, et al., "Why Do So Many Drugs for Alzheimer's Disease Fail in Development? Time for New Methods and New Practices?" J Alzheimers Dis., (2008), vol. 15, No. 2: 303-325.
Nair, et al., "A simple practice guide for dose conversion between animals and human," J Basic Clin Pharm., (2016), vol. 7: 27-31.
Song, "Rho Kinase Inhibitor Fasudil Protects against b-Amyloid-Induced Hippocampal Neurodegeneration in Rats," CNS Neuroscience & Therapeutics, (2013), vol. 19: 603-610.
Koch, et al., "ROCK inhibition in models of neurodegeneration and its potential for clinical translation," Pharmacology & Therapeutics, (2018), https://doi.org/10.1016/j.pharmthera.2018.03.008.
Roman, G.C., "The identity of lacunar dementia and Binswanger disease," Med Hypotheses, (1985), vol. 16(4) 389-91. Abstract only.
Roman, Gustavo C., "Facts, myths, and controversies in vascular dementia," J Neurol Sci., (2004), vol. 226: 49-52.
Wetterling, et al., "The ICD-10 Criteria for Vascular Dementia," Dementia, (1994), vol. 5: 185-188.
Wetterling, et al., "Comparison of Different Diagnostic Criteria for Vascular Dementia (ADDTC, DSM-IV, ICD-10, NINDS-AIREN)," Stroke, (1996), vol. 27: 30-36.
International Search Report and Written Opinion of International Patent Application No. PCT/US21/12587 dated Apr. 16, 2021.
Algase et al., "Biomechanical activity devices to index wandering behavior in dementia" American Journal of Alzheimer's Disease and Other Dementias, Mar./Apr. 2003, pp. 85-92, vol. 18, No. 2.
Jo et al., "The Effect of Cognitive Intervention on Cognitive Improvement in Patients with Dementia", Dementia and Neurocognitive Disorder, Mar. 2018, pp. 23-31, vol. 17, No. 1.
Vicari et al.,"Efficacy and Safety of Fasudil in Patients With Stable Angina A Double-Blind, Placebo-Controlled, Phase 2 Trial", Journal of the American College of Cardiology, Nov. 15, 2005, pp. 1803-1811, vol. 46, No. 10.
Pai et al., "Topographical disorientation in community-residing patients with Alzheimer's disease. International Journal of Geriatric Psychiatry", Feb. 16, 2004, pp. 250-255; vol. 19.

* cited by examiner

METHODS OF TREATING WANDERING IN LEWY DODY DEMENTIA

CROSS REFERENCE TO RELATED APPLICATION

This instant application claims priority to U.S. Provisional application No. 63/005,913, filed on Apr. 6, 2020, and to U.S. Provisional application No. 62/994,527, filed on Mar. 25, 2020, the contents of each of which are hereby incorporated by reference in their entireties.

BACKGROUND OF THE INVENTION

Wandering is "locomotion behavior having a frequent, repetitive, temporally-disordered, and/or spatially-disordered nature that is manifested in lapping, random, and/or pacing patterns some of which are associated with eloping, eloping attempts, or getting lost unless accompanied." Wandering behavior is associated with many conditions degenerative neurological conditions, such as Huntington's disease (HD), autism spectrum disorder, Down syndrome, progressive supranuclear palsy, corticobasal degeneration, and dementia. These neurological conditions often are pathologically linked to a proteinopathy—a aggregates or deposits usually consisting of mis-folded proteins. Huntington's disease, for example, is associated with aggregates of the huntingtin protein. Dementias are often associated aggregates with FUS, TDP-43, tau, and/or Abeta42.

The most common underlying cause of wandering is dementia. The dementia can result, for example, from Parkinson's Disease (PD), Huntington's Disease (HD), amyotrophic lateral sclerosis (ALS), Alzheimer's Disease (AD), Dementia with Lewy Bodies (DLB) and Frontotemporal Dementia (FTD), normal pressure hydrocephalus (NPH) and head injuries, among others. While wandering occurs in all forms of dementia, irrespective of etiology, it occurs at different frequencies and exhibits different quantitative and qualitative features depending on the type of dementia (Cipriani 2014). Wandering also occurs in other neurological disorders, such as autism spectrum disorder and Down syndrome.

There is no standardized assessment tool for diagnosing or assessing wandering. Wandering is frequently captured using the Neuropsychiatric Inventory (NPI) and the Cohen-Mansfield Agitation Inventory, two broad tools for assessing behavioral and psychological symptoms of dementia (Yayama 2013). As an example, the NPI has a single item on wandering: 'pace or wheel around the facility with no reason.' Thus, illustrating its limited utility, the NPI will only detect the repetitive wandering that is characteristic of FTD, but uncommon in AD and rare in VaD (Bathgate 2001; Nakaoko 2010). The Algase Wandering Scale (Algase 2001a), on the other hand, is the only tool for the exclusive assessment of wandering and it is not limited to a specific type/dimension of wandering (Yayama 2013).

Wandering can be described in terms of a variety of dimensions including frequency (persistence), pattern (lapping, random, or pacing), boundary transgressions (elopement), and deficits in navigation or wayfinding (spatial disorientation) (Algase 2001a). Thus, wandering is a general term used to describe many different actions and it is well documented that wandering quantitatively and qualitatively varies with different forms and degrees of dementia (Cipriani 2014).

Wandering is often the reason a dementia patient loses his/her independence and is placed in a long-term-care facility, which not only affects self-esteem and leads to social isolation, but also represents a significant societal cost (Logsdon 1998). Wandering is characterized by excessive, aimless ambulation that frequently leads to nuisance and, more importantly, safety concerns (Lai 2003; Aud 2004). Especially when the patient is able to escape his/her controlled environment, wandering increases the risk of quality of life-affecting injury through falls and other incidents, or even death (Algase 2001a; Wick 2006). Wandering patients have been reported to be "chemically" restrained using antipsychotics or sedation to prevent escape and to control problematic symptoms like wandering (Human Rights Watch 2018). Clearly a goal of any wandering treatment would be avoiding chemical restraint. There are currently no treatments available for wandering of any etiology and so there is a significant need for treatment approaches for wandering.

Among the dementias, VaD is differentiated from other forms of dementia by the presence of one or more vascular causes in the general absence of other pathologies. Specifically, VaD is not a neurodegenerative disease, unlike all other types of dementia (Salardini 2019). Uniquely, the pathophysiology of VaD is not linked to and underlying proteinopathy.

Kamei (1996) reported on using fasudil in two patients with wandering due to VaD. One patient was diagnosed with Binswanger-type cerebral infarction, confirmed by MM imaging. Prior to treatment, the patient had a history of more than 3.5 years of wandering symptoms, consisting primarily of wayfinding problems. The patient could not find his way home from visiting customers. Then, for about a year-and-a-half prior to beginning treatment, the patient was regularly eloping approximately 2-3 times per week. Within weeks of beginning treatment, wandering symptoms disappeared and remained absent for the duration of treatment. When the patient was removed from treatment, wandering symptoms reappeared within weeks. Upon re-treatment, wandering again resolved. The other patient was diagnosed with sequelae of cerebral bleeding and multiple lacunar infarctions, confirmed by MM. Approximately 5 months after the hemorrhage, the patient began exhibiting wayfinding symptoms, beginning with several episodes of losing his way with frequency increasing to 2-3 times per week over several months. Wandering symptoms disappeared quickly and remained absent for the duration of treatment, returning each time treatment was stopped. It should also be noted that Kamei 1996 presented two cognitive measures, the Mini Mental State Exam (MMSE) and the Hasegawa Dementia Score (HDS), which are very similar and usually yield very similar results. In fact, the HDS usually scores dementia patients as more severe than the MMSE (Kim 2005), yet not only were the MMSE scores in Kamei 1996a consistently worse than the HDS, the different scores lead to a dramatically different understanding of the patient population. The HDS suggests that the patients had only mild dementia, whereas the MMSE suggest that they are moderately to severely demented.

Kamei also published another paper in 1996 (Kamei 1996b) with substantially the same findings. Prior to these publications, Kamei filed a patent application in Japan (Patent Application 6-293643) based on the same two patients in the publication and a third patient.

Despite the preliminary results in a few patients with subcortical vascular dementia, there is no evidence that this observation, even if confirmed by a clinical study, could be extrapolated to wandering in other forms of dementia, especially dementia with proteinopathy as an underlying pathology, and certainly says nothing with respect to proteinopathy-associated wandering in general. Improvements based on treatment with a cardiovascular drug in wandering due to a cardiovascular pathology is not informative of the ability to affect wandering due to a completely different underlying pathology.

The etiologies, pathologies and symptoms of sub-cortical and dementias of the cortex (i.e., most proteinopathy-associated dementia) are well characterized. Cortical and sub-cortical dementia tend to produce different kinds of deficits. Characteristic symptoms of subcortical dementia typically include forgetfulness, slowing of thought processes, mild intellectual impairment, apathy, inertia, depression (sometimes with irritability), loss of recall ability, and the inability to manipulate knowledge. Additionally, subcortical dementia patients have mood disorders. Other behavioral abnormalities like repetitive and compulsive behavior occur in some patients suffering from subcortical dementia. Generally, sub-cortical dementia presentation is more subtle and temporally progressive, often described as defects in executive function in sub-cortical dementia. This includes deficits in speed and "strategic" processing (i.e., attention, planning, and monitoring) in tasks such as memory tasks.

In contrast, cortical dementia is caused by multi-infarcts in the cortex, and symptoms include aphasia (loss of speech), amnesia, agnosia, and apraxia.

Memory is impaired in both sub-cortical and cortical vascular dementia. But in cortical vascular dementias, the recall abnormality is due to a failure to encode information properly or decay of memory consolidation. In contrast, subcortical disorders exhibit deficits in spontaneous recall, but encoding and storage are largely preserved, and recollection can be aided. Also, in cortical dementia severe retrograde amnesia with a marked temporal gradient often co-exists with a general semantic memory deficit that arises from damage to cortical association areas. While earlier memories may be preserved, later memories are not. In contrast, in subcortical disorders exhibit deficits in spontaneous recall, but encoding and storage are largely preserved, and recollection can be aided. Subcortical dementia is characterized by a relatively mild retrograde amnesia that equally affects all time periods because here there is faulty retrieval of successfully stored information. It is the recall deficit that resulted in wayfinding problems in sub-cortical vascular dementia.

Sub-cortical and cortical dementia are differentially diagnosed. White matter hyperintensities (i.e., sub-cortical) are detected using magnetic resonance imaging and are considered to result from cerebral small vessel disease, especially the larger volume lesions. This damage can be quantified using the Fazekas scale: 0 (no lesions); 1 (punctiform lesions); 2 (early confluent lesions); and 3 (confluent lesions). A Fazekas score of 1 can be considered normal, whereas scores 2 and 3 indicate the presence of small vessel disease. A score of 3 is abnormal at any age. The presence of confluent lesions in the frontal and parietal lobes is indicative of a large white matter pathology (>25%) and can be used in making a diagnosis of (subcortical) vascular dementia. Lacunar infarcts involving multiple basal ganglia and the frontal white matter, as well as bilateral thalamic lesions are also diagnostic of subcortical vascular dementia.

Strategic large vessel infarctions can indicate cortical dementia when they involve the following territories: bilateral anterior cerebral artery, paramedian thalamic, inferior medial temporal lobe, parieto-temporal and temporo-occipital association areas and angular gyms, superior frontal and parietal watershed areas in the dominant hemisphere.

A central issue with interventions that target dementia is that of association versus causation. In order for an intervention to work in treating a disease, it must interrupt the chain of causation. AD, the most common form of dementia, provides a very instructive case. The two characteristic pathological findings of AD are the extracellular amyloid plaques and inter-neuronal neurofibrillary tangles (NFT).

While Aβ, tau and neuroinflammation are certainly associated with AD, is it not clear they are involved in causation and thus, it is unclear that affecting any of these will have any therapeutic benefit in treating the disease. Based on understanding the familial disease, it is believed that Aβ starts the process of neurodegeneration by inducing Tau pathology, neuroinflammation and finally the neuronal loss that leads to cognitive decline. In other words, Aβ is at the beginning of the causality chain. Stopping Aβ pathology should stop the disease and, so far, most therapeutic approaches have targeted Aβ.

Despite the overwhelming literature showing the promise of targeting Aβ in animal models, however, there have been no products that have been shown to work in AD (Ceyzériat 2020). These failures include, notably among many, Anti-Aβ42+Freud's adjuvant, Bapineuzumab, Solanezumab, Aducanumab, Verubecestat, Lanabecestat, Atabecestat, CNP520, Elenbecestat, γ-Secretase inhibitors, Bryostatin and PBT2.

Tau is a less likely target because of the evidence that it is downstream of AP, and thus is not causative, and so trials have been less frequent. Notably, of 15 trial targeting tau that have been initiated, already four of them have been stopped.

The role of neuroinflammation, the third putative interventional target, in AD is unclear, likely being beneficial in early-stage disease, but possibly evolving to a bad actor by participating in a loop of pro-inflammatory cytokine production and oxidative stress. While epidemiological studies have suggested that treatment with nonsteroidal anti-inflammatory drugs (NSAIDs) reduce the risk of developing AD and they can decrease amyloid load in transgenic models, to date prospective studies testing anti-inflammatory drugs have shown no beneficial effect on cognition in AD. Studies targeting neuroinflammation are ongoing, but early results are not promising. Neflamapimod, a selective inhibitor of p38 mitogen-activated protein kinase showed efficacy in an animal model, but it had no effect on Aβ deposition in humans and failed its primary endpoint of improving episodic memory in Phase 2, despite reducing tau in the cerebrospinal fluid.

In view of the number of clinical failures of compounds that seemed promising in animal models, a grave degree of skepticism should be applied in interpreting animal data. Even aside from the obvious issues of differences in brain complexity between rodents and humans, many of the existing models bear only a passing resemblance to the human condition. Many things can cause neural degeneration in animals and many putative drugs can halt that neural degeneration, but the underlying pathophysiology and chain of causation is unknown and it is there that a disease modifying intervention must act. It is crucial, therefore, that animal models, with their known deficiencies in the best of cases, as closely resemble the human disease as possible, in both pathology and clinical presentation.

There are a number of publications looking at the use of rho kinase inhibitors in various models of AD/dementia. Most models are deficient in basic properties. Some models involve the direct induction of neurotoxicity with agents like streptozotocin or even by direct injection of amyloid-beta into the brain. While these models may exhibit certain AD-like properties, they are basically just models of neural degeneration and cannot predict treatment of AD itself. Even the transgenic models are deficient. For example, there are a number of transgenic mice that only develop amyloid plaques without NFTs, such as the APP/PS-1 mouse, perhaps the most widely reported transgenic model. There are also mice that develop tauopathies, without amyloid plaques, such as the rTG4510 tau mouse. AD is characterized by the presence of both. Some publications use unrealistic routes of administration (e.g., intraventricular injection) and many do not use appropriate dosing. In this regard, standard formulas exist for converting doses used in animals to the same dose in humans. Human equivalent dose (HED) can be calculated, for example, using Table 1 of Nair & Jacob, *J Basic Clin Pharm.* 7:27-31 (2016), which are the same conversions used by the US FDA. Becker, *Alzheimers Dis.* 15:303-325 (2008) discusses the criticality of dose in successful AD drug development and points to it as a failure point in AD drug development.

Published literature exists in which fasudil is administered in animal models of dementia. But these studies are deficient for many of the same reasons. Namely, the animal models do not faithfully recapitulate human disease, partly due to species differences in neuroanatomy (Sasaguri 2017) and partly due to the deficient basic pathological bases of the models, described above. In addition, some fail to use physiologically relevant doses and, importantly, no outcomes relevant to wandering were measured in any of them. It is important also to note that the hallmark of onset in the paradigmatic cortical dementia, AD, is the failure of semantic memory, which cannot be measured in any animal model and so all animal models share this deficiency as well. For example, Hamano et al., 2019, administered 12 mg/kg/day (68 mg HED) to rTG4510 tau transgenic mice and measured only tau phosphorylation/cleavage and oligomers, but no outcomes. Elliott 2018 used a triple transgenic mouse model (APP Swedish, MAPT P301L, and PSEN1 M146V) and observed reduce ß-amyloid plaques in vivo at a dose of 10 mg/kg/day (intraperitoneally) fasudil (57 mg RED). Sellers 2018 used the AB42 mouse model and administered fasudil intraperitoneally at a dose of 10 mg/kg BID (226 mg HED) but monitored only ß-amyloid dendritic spine loss. Couch et al. 2010 used intraventricular infusion and observed effects on dendritic branching and no outcomes relevant to wandering. Putting aside the absence of any behavioral outcomes in these references, intraventricular administration is not a therapeutic option for humans. Yu 2017 and Hou 2012 administered fasudil at 5 and 10 mg/kg/day intraperitoneally to APP/PS1 transgenic mice (70, 140 mg HED) and streptozotocin rats (226 mg HEM, respectively and observed that latency distance and quadrant time were improved in the Morris water maze (a model for spatial learning and memory, not wandering). There is no clear link between memory loss and wandering as not all patients with cortical dementia wander.

Conflicting reports to the above also exist. For example, Turk 2018 (dissertation) used triple transgenic mice and did not observe improvements in spatial memory at 10 or 12 months of age with fasudil administered in water at 30 mg/kg and 100 mg/kg.

Based on currently available animal modeling, different therapeutic strategies targeting the pathological hallmarks of dementia have been tested but have failed to show any beneficial effects in humans. At present, available medications are limited to acetylcholinesterase inhibitors and N-methyl-D-aspartate (NMDA) receptor antagonists, which show only modest improvements in some cognitive symptoms. No existing or even proposed therapies address the problem of wandering in dementia. There exists a significant unmet need to provide new, therapies that show benefit in humans, not just animals.

SUMMARY OF THE INVENTION

In one embodiment, the invention provides a method of treating a patient with proteinopathy-associated disease. Further to this embodiment, methods of treating such wandering are provided that involved administering a therapeutically effective amount of a rho kinase inhibitor.

Some embodiments involve treating wandering in patients with Huntington's disease or patients with dementia. Treating wandering in patients with dementia due to Alzheimer's disease or frontotemporal dementia is preferred. Some embodiments involve treating wandering in patients with dementia with Lewy bodies, a head injury, Parkinson's disease, autism spectrum disorder, Down syndrome, normal pressure hydrocephalus, Creutzfeldt-Jakob dementia and posterior cortical atrophy.

In certain aspects of this embodiment, the patient does not have vascular dementia, including sub-cortical dementia. In another embodiment, the patient has mixed dementia (vascular dementia associated with proteinopathy-associated dementia). In another embodiment, the patient does not have mixed dementia.

In a specific embodiment, the patient is male. In another specific embodiment, the patient has early-onset dementia. In a specific embodiment, the patient has a defect in a presenilin-1 gene, an amyloid precursor protein (APP) gene, and/or a presenilin 2 gene. In a further embodiment, the patient has at least one ApoE4 allele.

In a further embodiment, the patient treated has inflammatory-associated proteinopathy disease, such as increases in C-reactive protein or increased serum albumin to globulin ratio.

In a further embodiment, the patient treated has non-inflammatory associated proteinopathy disease.

In another embodiment, the patient treated has limbic-predominant associated proteinopathy disease. In a further embodiment, the limbic-predominant patient is a female.

In another embodiment, the patient treated has proteinopathy primarily in the hippocampal region of the brain. In another embodiment, the patient to be treated has proteinopathy primarily in the cortical region of the brain and not the hippocampal region. In a specific embodiment, the hippocampal-spared patient is male. In one embodiment, the patient treated has a defect in, or differential expression of an SNCA, LRRK2, Parkin, PINK1, DJ1, VPS35 and/or ATP13A2 gene. In another specific embodiment, the patient treated with fasudil has at least one ApoE ε4 allele.

In another embodiment, the patient treated exhibits motor impairment symptoms. In another embodiment, the patient treated exhibits non-motor symptoms. In a further embodiment the patient treated exhibits both motor—impairment and non-motor symptoms. In another embodiment, the patient to be treated does not exhibit hypokinesia.

In yet another embodiment, the patient to be treated exhibits chorea.

In another embodiment, the patient to be treated exhibits psychosis including hallucinations and delusions.

In preferred embodiments of the invention, the rho kinase inhibitor is an isoquinoline derivative, such as fasudil, its primary metabolite M3, or salts, or derivatives thereof.

In certain embodiments of the invention, the methods of treatment are sustained for minimum time periods. In one preferred embodiment, treatment continues for at least 6 months.

Still other embodiments contemplate doses exceeding 60 mg per day in immediate-release form, with preferred dosing occurring in three equal portions throughout the day. The most preferred total daily dose is between 70 mg and 120 mg, with 90 mg per day especially preferred.

Further embodiments of the invention relate to treating patients with a proteinopathy characterized by deposits containing the huntingtin protein, FUS, TDP-43, tau, amyloid-(including Abeta42), optineurin, ubiquitin 2, superoxide dismutase 1, neurogenic locus notch homolog protein 3 (NOTCH3) and/or α-synuclein.

In another embodiment, the invention includes a method of treating a patient with senile dementia of the Alzheimer's type (SDAT). In a preferred embodiment, the patient exhibits deficits in parietal function.

In a further embodiment, the invention includes a method of treating a patient wherein progression from wayfinding defects to elopement, escape or boundary transgressions is delayed or prevented upon treatment with fasudil. In another embodiment the invention includes a method of treating a patient for wandering, wherein the treatment eliminates use of chemical restraints such as use of antipsychotic medications (e.g., aripiprazole, clozapine, haloperidol, olanzapine, quetiapine, risperidone and ziprasidone).

In another embodiment, the patient to be treated for wandering has recently been placed into an unfamiliar environment, such as removed from home into a care facility.

In a further embodiment, the patient treated has recently undergone a change in medication including neuroleptic medications, especially those that induce akathisia.

In another embodiment, the patient to be treated for wandering has a history of depression, anxiety, or schizophrenia.

In one embodiment, the patient treated has chronic insomnia.

In a further embodiment, the patient treated has restless leg syndrome.

In certain embodiments, subjects with emotional incontinence, compulsive laughter and/or crying are excluded.

DETAILED DESCRIPTION OF THE INVENTION

The invention is based on the discovery that rho kinase inhibitors can be used to treat wandering associated with an underlying proteinopathy. Proteinopathy is associated with many neurological diseases that frequently, but not always, lead to dementia. The invention, therefore, contemplates treating wandering behavior associated with many degenerative neurological conditions, such as Huntington's disease (HD), Parkinson's disease (PD), autism spectrum disorder, Down syndrome, and dementia (for example Alzheimer's disease, frontotemporal dementia, dementia with Lewy Bodies, Creutzfeldt-Jakob dementia (CJD), normal pressure hydrocephalus, HD dementia and PD dementia). These neurological conditions often are pathologically linked to a proteinopathy—aggregates or deposits usually consisting of mis-folded proteins. Huntington's disease, for example, is associated with aggregates of the huntingtin protein. Dementias are often associated aggregates with FUS, TDP-43, tau, and/or amyloid-β.

ROCK Inhibitors

The inventive methods contemplate the administration of a rho kinase (ROCK) inhibitor in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

A large number of pharmacological ROCK inhibitors are known (Feng, LoGrasso, Defert, & Li, 2015). Isoquinoline derivatives are a preferred class of ROCK inhibitors. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms. In vivo, fasudil is subjected to hepatic metabolism to its active metabolite hydroxyfasudil (aka, M3). Other examples of isoquinolone derived ROCK inhibitors include dimethylfasudil and ripasudil.

Other preferred ROCK inhibitors are based on based on 4-aminopyridine structures. These were first developed by Yoshitomi Pharmaceutical (Uehata et al., 1997) and are exemplified by Y-27632. Still other preferred ROCK inhibitors include indazole, pyrimidine, pyrrolopyridine, pyrazole, benzimidazole, benzothiazole, benzathiophene, benzamide, aminofurazane, quinazoline, and boron derivatives (Feng et al., 2015). Some exemplary ROCK inhibitors are shown below:

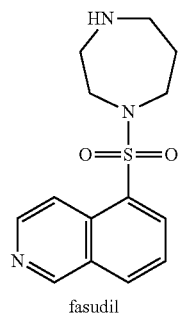

fasudil

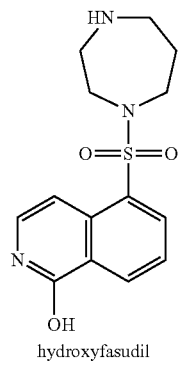

hydroxyfasudil

-continued

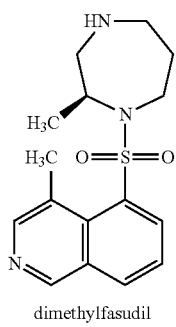
dimethylfasudil

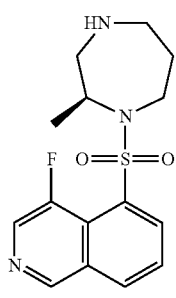
ripasudil

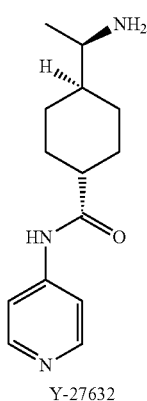
Y-27632

ROCK inhibitors according to the invention may have more selective activity for either ROCK1 or ROCK2 and will usually have varying levels of activity on PKA, PKG, PKC, and MLCK. Some ROCK inhibitors may be highly specific for ROCK1 or ROCK2 and have much lower activity against PKA, PKG, PKC, and MLCK.

A particularly preferred ROCK inhibitor is fasudil. Fasudil may be exist as a free base or salt and may be in the form of a hydrate, such as a hemihydrate.

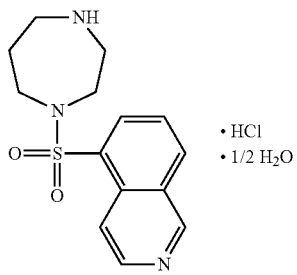 [SMILES: O=S(=O)(c1cccc2cnccc12)N1CCCNCC1]

Hexahydro-1-(5-isoquinolinesulfonyl)-1H-1,4-diazepine monohydrochloride hemihydrate Fasudil is a selective inhibitor of protein kinases, such as ROCK, PKC and MLCK and treatment results in a potent relaxation of vascular smooth muscle, resulting in enhanced blood flow (Shibuya 2001). A particularly important mediator of vasospasm, ROCK induces vasoconstriction by phosphorylating the myosin-binding subunit of myosin light chain (MLC) phosphatase, thus decreasing MLC phosphatase activity and enhancing vascular smooth muscle contraction. Moreover, there is evidence that fasudil increases endothelial nitric oxide synthase (eNOS) expression by stabilizing eNOS mRNA, which contributes to an increase in the level of the potent vasodilator nitric oxide (NO), thereby enhancing vasodilation (Chen 2013).

Fasudil has a short half-life of about 25 minutes, but it is substantially converted in vivo to its 1-hydroxy (M3) metabolite. M3 has similar effects to its fasudil parent molecule, with slightly enhanced activity and a half-life of about 8 hours (Shibuya 2001). Thus, M3 is likely responsible for the bulk of the in vivo pharmacological activity of the molecule. M3 exists as two tautomers, depicted below:

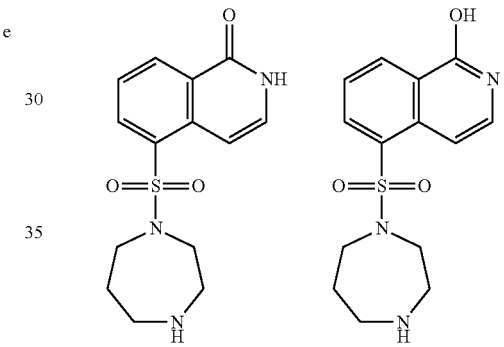

The ROCK inhibitors used in the invention, such as fasudil, include pharmaceutically acceptable salts and hydrates. Salts that may be formed via reaction with inorganic and organic acid. Those inorganic and organic acids are included as following: hydrochloric acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

Pharmaceutical Compositions

Pharmaceutical compositions of ROCK inhibitors usable in the are generally oral and may be in the form of tablets or capsules and may be immediate-release formulations or may be controlled- or extended-release formulations, which may contain pharmaceutically acceptable excipients, such as corn starch, mannitol, povidone, magnesium stearate, talc, cellulose, methylcellulose, carboxymethylcellulose and similar substances. A pharmaceutical composition comprising a ROCK inhibitor and/or a salt thereof may comprise one or more pharmaceutically acceptable excipients, which are known in the art. Formulations include oral films, orally disintegrating tablets, effervescent tablets and granules or beads that can be sprinkled on food or mixed with liquid as a slurry or poured directly into the mouth to be washed down.

Pharmaceutical compositions containing ROCK inhibitors, salts and hydrates thereof can be prepared by any method known in the art of pharmaceutics. In general, such preparatory methods include the steps of bringing a ROCK inhibitor or a pharmaceutically acceptable salt thereof into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition used in accordance with the methods of the present invention may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition used in the methods of the present invention may comprise a diluent. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

In certain embodiments, the pharmaceutical composition used in the methods of the present invention may comprise a granulating and/or dispersing agent. Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

In certain embodiments, the pharmaceutical composition used in the methods of the present invention may comprise a binding agent. Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

In certain embodiments, the pharmaceutical composition used in the methods of the present invention may comprise a preservative. Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

In certain embodiments, the pharmaceutical composition used in the methods of the present invention may comprise an antioxidant. Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

In certain embodiments, the pharmaceutical composition used in the methods of the present invention may comprise a chelating agent. Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the pharmaceutical composition may comprise a buffering agent together with the ROCK inhibitor or the salt thereof. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, the pharmaceutical composition used in the methods of the present invention may comprise a lubricating agent. Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

In other embodiments, the pharmaceutical composition of containing a ROCK inhibitor or salt thereof will be administered as a liquid dosage form. Liquid dosage forms for oral and parenteral administration include pharmaceutically acceptable emulsions, microemulsions, solutions, suspensions, syrups, and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Some compositions of the invention relate to extended- or controlled-release formulations. These may be, for example, diffusion-controlled products, dissolution-controlled products, erosion products, osmotic pump systems or ionic resin systems. Diffusion-controlled products comprise a water-insoluble polymer which controls the flow of water and the subsequent egress of dissolved drug from the dosage from. Dissolution-controlled products control the rate of dissolution of the drug by using a polymer that slowly solubilizes or by microencapsulation of the drug—using varying thicknesses to control release. Erosion products control release of drug by the erosion rate of a carrier matrix. Osmotic pump systems release a drug based on the constant inflow of water across a semi permeable membrane into a reservoir which contains an osmotic agent. Ion exchange resins can be used to bind drugs such that, when ingested, the release of drug is determined by the ionic environment within the gastrointestinal tract.

Methods of Treatment

The invention contemplates treating wandering in diseases with an underlying proteinopathy, including Huntington's disease, autism spectrum disorder, Down syndrome, and dementia. Proteinopathy-associated dementia can result, for example, from Alzheimer's Disease (AD), Dementia with Lewy Bodies (DLB), Frontotemporal Dementia (FTD), head injuries, normal pressure hydrocephalus, Creutzfeldt-Jakob disease, amyotrophic lateral sclerosis and Parkinson's disease among others. Thus, in the case where wondering occurs in a neurological condition associated with a proteinopathy, such as the aforementioned, for the purposes of the invention this is considered to be proteinopathy-associated wandering and, therefore, treatable according to the invention.

The most common underlying cause of proteinopathy-associated wandering is dementia. Dementia is not itself a disease, but rather defines a set of symptoms related to a decline in memory and/or cognitive skills of such severity to adversely impact activities of daily living (Bruun 2018). Recognizing this, the definitive classification of dementia is based on the underlying neuropathology (Elahi 2017). With the exception of vascular dementia (VaD), dementia is considered a neurodegenerative disease.

The primary neurodegenerative dementias AD, DLB, Parkinson's Disease dementia, FTD, and dementia associated with prion diseases (like CJD) are characterized by progressive proteinopathy, which is an accumulation of misfolded proteins that lead to neuronal loss, neuroinflammation and glial reaction. Neurodegenerative dementias are differentiated by the location and nature of misfolded protein accumulation. Thus, an understanding of the applicable underlying pathology of the dementia is essential to inform rational treatment of what are considered different underlying conditions.

The inventive methods relate to treating wandering associated with an underlying proteinopathy. Proteinopathy-associated dementia, as used herein, refers to any form of dementia in which proteinopathy is considered to be part of the pathophysiology of the dementia. Proteinopathy, as recognized by one skilled in the art, refers to lesions that consist of aggregates or deposits of protein that are not present in normal tissues. Alzheimer's disease, for instance, is associated with amyloid plaques, consisting of aggregates of Abeta4, and fibrillary tangles, consisting of deposits of phosphorylated tau. Frontotemporal dementia is associated with deposits of tau, TDP-43 and/or FUS. On the other hand, pure vascular dementia is not associated with proteinopathy. Accordingly, Alzheimer's disease and frontotemporal dementia are included within the scope of the invention, but pure vascular dementia is not. The invention specifically contemplates treating wandering in patients with conditions associated with abnormal deposits of huntingtin protein, FUS, TDP-43, tau, amyloid-β (including Abeta42), optineurin, ubiquitin 2, superoxide dismutase 1, neurogenic locus notch homolog protein 3 (NOTCH3) and/or α-synuclein.

Diagnosis of proteinopathy-associated dementia can be done using imaging and measuring biomarkers in cerebrospinal fluid (CSF). The most widely used CSF biomarkers for Alzheimer's disease measure certain proteins: beta-amyloid 42 (the major component of amyloid plaques in the brain), tau, and phospho-tau (major components of tau tangles in the brain). In Alzheimer's disease, beta-amyloid 42 levels in CSF are low, and tau and phospho-tau levels are high, compared with levels in people without Alzheimer's or other causes of dementia.

Imaging is as useful tool in diagnosing dementia, in particular computerized tomography (CT), magnetic resonance imaging (MM) and positron emission spectroscopy (PET). Neural degeneration results in brain atrophy and this can be detected and quantified. Automated tools are increasingly available that can perform these functions.

Fluorodeoxyglucose (FDG) PET scans measure glucose use in the brain. Glucose, a type of sugar, is the primary source of energy for cells. Studies show that people with dementia often have abnormal patterns of decreased glucose use in specific areas of the brain. An FDG PET scan can show a pattern that may support a diagnosis of a specific cause of dementia.

Amyloid PET scans measure abnormal deposits of a protein called beta-amyloid. Higher levels of beta-amyloid are consistent with the presence of amyloid plaques, a hallmark of Alzheimer's disease. Several tracers may be used for amyloid PET scans, including florbetapir, flutemetamol, florbetaben, and Pittsburgh compound B.

Tau PET scans detect abnormal accumulation of a protein, tau, which forms tangles in nerve cells in Alzheimer's disease and many other dementias. Several tau tracers, such as AV-1451, PI-2620, and MK-6240, are being studied in clinical trials and other research settings.

Just as dementia is not a single condition, the wandering that results from the various underlying forms of dementia clearly is not a single condition. Wandering is not a simple function of cognitive decline. In fact, while cognitive impairment is correlated with frequency of wandering cycles, it is not correlated with the other domains of wandering (Algase 2001b). Several lines of evidence demonstrate that wandering is a reflection of the specific underlying pathology of the type, or even sub-type, of dementia.

First, wandering is more prevalent in certain types of dementia than others. Cooper (1993) found in a study of 1312 dementia patients that wandering occurred in 26% of AD patients versus 17% in VaD, the difference reaching statistical significance, and that while the severity of wandering is associated with progression of dementia, the higher prevalence of wandering in AD versus VaD was consistent among early-, mid- and late-stages of disease. Confirming the difference in wandering rate among different forms of dementia, in a study of 638 community-residing dementia patients, Klein (1999) observed wandering in 14.1% of VaD patients and 21.4% in AD. Knuffman (2001) found that wandering was much more common in DLB than in AD.

Second, differences in wandering patterns in different forms of dementia indicate grounding in different pathologies. Routinized wandering, like repetitive pacing and lapping, is very common in FTD and rare in AD, in which wandering tends to be unpatterned; patterned wandering in VaD is even more rare than in either AD or FTD (Bathgate 2001). Repetitive pacing and lapping, evolving to a fixed route in advanced disease, are strongly predictive of FTD and can be used to help distinguish FTD from AD (Nakaoka 2010). Moreover, AD patients get lost outside of their homes at a much higher rate than VaD patients (41% versus 20%) (Ballard 1991).

Even between forms of AD, patterns can differ. Nakaoka (2010) observed that excessive (>10 km per day), non-patterned wandering was limited to early-onset AD patients with significant levels of cognitive impairment.

Wandering generally can be characterized by two domains. The first domain is movement, generally in the form of ambulation unless the patient is disabled and, for example, confined to a wheelchair. The second domain is problematic behavior, usually in the form of boundary transgressions and/or wayfinding problems. However, it could be reflected in the movement itself, such as pacing or lapping behavior. It may involve inappropriately following a caregiver. A common problematic behavior is attempted escape or elopement. A certain quantity of movement may also be considered the problematic behavior. A normal person is in motion approximately 10% of their waking hours and so movement beyond this threshold amount can be considered problematic behavior. A patient will be considered to suffer from wandering when in motion for at least 20% of their waking hours, but preferably more than 30% of their waking hours. As a patient spends more time in motion, the behavior becomes particularly problematic because they risk exhaustion and, therefore, falling and serious injury. Thus, some wandering patients are in motion more that 40% or 50% of their waking hours and some more than 60%, 70% or even 80%.

It has been proposed that wandering can be persistent or sporadic and the present methods may be used to treat either population. Persistent wanderers exhibit excessive movement nearly every day, typically at least 4-5 days per week. On the other hand, sporadic wanderers do not exhibit excessive movement, but rather they are generally sedentary with occasional movement, typically associated with elopement, boundary transgressions, escape or wayfinding defects. Sporadic wanders may exhibit the behavior as infrequently as monthly or as frequently as 2, 3 or even 4, 5, 6, or more times per week. Unlike the persistent wanderer, the sporadic wonderer does not spend an abnormally high amount of time in motion.

In one specific embodiment, treatment with fasudil reduces the amount of repetitive movement wandering (e.g., lapping, pacing) in the patients by at least 10%; 15%; 20%; 25%; 30%; 35%; 40%; 45% or 50%. In another embodiment, treatment with fasudil reduces the amount repetitive movement wandering by 50% or more. In preferred embodiments, treatment with fasudil reduces repetitive movement by at least 75%. In a preferred embodiment, treatment with fasudil reduces the amount of repetitive movement wandering to the normative 10% motion during waking hours.

In a further embodiment, treatment with fasudil reduces the number of times per day repetitive movement wandering occurs by at least one time, preferably by at least two times, and more preferably by at least three times per day.

In a further embodiment, treatment with fasudil reduces the number of days repetitive movement wandering occurs by at least one day per week, preferably by at least two days per week, and more preferably by at least three days per week.

In another specific embodiments, treatment with fasudil reduces persistent wandering by at least 10%; 15%; 20%; 25%; 30%; 35%; 40%; 45% or 50%. In another embodiment, treatment with fasudil reduces persistent wandering by 50% or more. In preferred embodiments, treatment with fasudil hydrochloride hemihydrate reduces persistent wandering by at least 75%. In a preferred embodiment, treatment with fasudil reduces persistent wandering to the normative 10% motion during waking hours.

In a further embodiment, treatment with fasudil reduces the number of days wandering occurs in persistent wandering by at least one day per week, preferably by at least two days per week, and more preferably by at least three days per week.

In another embodiment, treatment with fasudil reduces sporadic wandering. by at least 10%; 15%; 20%; 25%; 30%; 35%; 40%; 45% or 50%. In another embodiment, treatment with fasudil reduces sporadic wandering by 50% or more. In preferred embodiments, treatment with fasudil reduces sporadic wandering by at least 75%. In a preferred embodiment, treatment with fasudil reduces sporadic wandering to the normative 10% motion during waking hours.

In another embodiment, treatment with fasudil reduces pacing or lapping by at least 10%; 15%; 20%; 25%; 30%;

35%; 40%; 45% or 50%. In another embodiment, treatment with fasudil reduces pacing or lapping by 50% or more. In preferred embodiments, treatment with fasudil reduces pacing or lapping by at least 75%.

In another embodiment, treatment with fasudil reduces eloping behavior by at least 10%; 15%; 20%; 25%; 30%; 35%; 40%; 45% or 50%. In another embodiment, treatment with fasudil reduces eloping behavior by 50% or more. In preferred embodiments, treatment with fasudil reduces eloping behavior by at least 75%.

In another embodiment, treatment with fasudil reduces spatial disorientation by at least 10%; 15%; 20%; 25%; 30%; 35%; 40%; 45% or 50%. In another embodiment, treatment with fasudil reduces spatial disorientation by 50% or more. In preferred embodiments, treatment with fasudil reduces spatial disorientation by at least 75%.

In another embodiment, treatment with fasudil reduces the caregiver burden associated with wandering by at least 10%; 15%; 20%; 25%; 30%; 35%; 40%; 45% or 50%. In another embodiment, treatment with fasudil reduces the caregiver burden associated with wandering by 50% or more. In preferred embodiments, treatment with fasudil reduces the caregiver burden associated with wandering by at least 75%.

In another embodiment, treatment with fasudil reduces the caregiver burden associated with one or more of persistent wandering, pacing, elopement and spatial disorientation by at least 10%; 15%; 20%; 25%; 30%; 35%; 40%; 45% or 50%. In another embodiment, treatment with fasudil reduces the caregiver burden associated with one or more of persistent wandering, pacing, elopement and spatial disorientation by 50% or more. In preferred embodiments, treatment with fasudil reduces the caregiver burden associated with one or more of persistent wandering, pacing, elopement and spatial disorientation by at least 75%.

In a further embodiment, treatment with fasudil reduces the number of days wandering occurs in sporadic wandering by at least one day per week, preferably by at least two days per week, and more preferably by at least three days per week.

In another embodiment, treatment with fasudil reduces the wandering occurs during sundowning, or early evening. In another embodiment, treatment with fasudil reduces the wandering occurs during the overnight hours. In one embodiment, the amount of wandering to determine the reduction can be measured using electronic motion and/or activity tracking device, including fitness trackers such as Fitbits. The fitness trackers can be used alone or in combination with GPS devices to measure location.

The Revised Algase Wandering Scale (Long Term Care Version) is a preferred instrument for measuring wandering (Nelson and Algase). It is divided into three different domains based on the three main wandering typologies: Persistent Wandering (PW); Eloping Behavior (EB); and Spatial Disorientation (SD). Each domain evaluates individual items on a scale that can be quantified with a score from 1-4.

An overall domain score is calculated based on the number of questions with a valid response. Thus, the individual scores are added up and divided by the number of questions in the domain with valid responses. It is highly preferred that at least 75% of the items in a domain have valid responses. The result will be a score from 1 to 4.

Likewise, an overall scale score may be obtained by averaging each of the 3 domains, resulting in a global score of 1-4. Alternatively, for the highest level of granularity, each individual item within a domain may be assessed individually.

The RAWS can be filled out by staff or a caregiver.

The PW domain consists of 9 individual items that look at the amount of spontaneous walking in absolute terms and relative to other similarly situated patients, pacing and restless walking (which may indicate agitation) and the timing of the wandering relative to mealtimes, which may be indicative of provocation to wander.

The EB domain consists of 4 items. It measures running off, entering unauthorized areas, leaving authorized areas and returns to authorized areas after an unnoticed leaving.

The SD domain consists of 6 items that assess getting lost, aimless walking, running into people and objects and the inability to locate certain rooms.

In certain embodiments, patients treated according to the invention will show improvements in at least 1 item of the RAWS. In preferred embodiments, patients will show improvements in at least one domain of the RAWS. In particularly preferred embodiments, patients will show improvements in the PW and/or the EB domain of the RAWS. Such improvements will generally be in the range of 10%; 15%; 20%; 25%; 30%; 35%; 40%; 45% or 50%.

| REVISED ALGASE WANDERING SCALE |
| --- |
| PERSISTENT WALKING (PW) |

1. Resident has a reduced amount of spontaneous walking
   ☐ walks the same or more as others of the same age and ability
   ☐ walks less than others of same age and ability
   ☐ walks only minimally, e.g. to go to bathroom
   ☐ does not walk spontaneously unless prompted
2. Resident has an increased amount of spontaneous walking
   ☐ walks about the same as others of same age and ability
   ☐ walks distinctly more than average, but will sit for periods
   ☐ walks distinctly more than average, rarely sits
   ☐ walks distinctly more than average, never sits
3. Resident walks about on their own
   ☐ only if prompted
   ☐ occasionally during the day
   ☐ frequently during the day
   ☐ almost constantly during the day
4. Resident walks around restlessly
   ☐ never
   ☐ on a few occasions
   ☐ regularly but not daily
   ☐ on a daily basis
5. Resident paces up and down
   ☐ never
   ☐ on a few occasions
   ☐ regularly but not daily
   ☐ on a daily basis
6. Resident walks around after awakening but before breakfast
   ☐ never
   ☐ less than others of same age and ability
   ☐ the same as others of the same age and ability
   ☐ more than others of same age and ability
7. Residents walks around between breakfast and lunch
   ☐ never
   ☐ less than others of same age and ability
   ☐ the same as others of the same age and ability
   ☐ more than others of same age and ability
8. Resident walks around between lunch and dinner
   ☐ never
   ☐ less than others of same age and ability
   ☐ the same as others of the same age and ability
   ☐ more than others of same age and ability
9. Resident walks around after dinner but before bedtime
   ☐ never
   ☐ less than others of same age and ability
   ☐ the same as others of the same age and ability
   ☐ more than others of same age and ability -continued

| REVISED ALGASE WANDERING SCALE |
| --- |
| ELOPING BEHAVIOUR (EB) |

10. Resident attempts to leave their authorised area
    ☐ never
    ☐ on a few occasions
    ☐ regularly but not daily
    ☐ on a daily basis
11. Resident runs off
    ☐ never
    ☐ on a few occasions
    ☐ regularly but not daily
    ☐ on a daily basis
12. Resident enters unauthorised areas
    ☐ never
    ☐ on a few occasions
    ☐ regularly but not daily
    ☐ on a daily basis
13. Resident was returned to authorised area after leaving unnoticed
    ☐ never
    ☐ only once
    ☐ more than once, but not often
    ☐ often

SPATIAL DISORIENTIATION (SD)

14. Resident gets lost
    ☐ never
    ☐ on a few occasions
    ☐ regularly but not daily
    ☐ on a daily basis
15. Resident cannot locate bathroom without help
    ☐ requires no help
    ☐ sometimes requires help
    ☐ usually requires help
    ☐ always required help
16. Resident cannot locate dining room without help
    ☐ requires no help
    ☐ sometimes requires help
    ☐ usually requires help
    ☐ always required help
17. Resident cannot locate own room without help
    ☐ requires no help
    ☐ sometimes requires help
    ☐ usually requires help
    ☐ always required help
18. Resident walks about aimlessly
    ☐ always has an identifiable destination/goal
    ☐ usually has an identifiable destination/goal
    ☐ sometimes has an identifiable destination/goal
    ☐ never has an identifiable destination/goal
19. Whilst walking alone, resident bumps into obstacles or other people
    ☐ never
    ☐ on a few occasions
    ☐ regularly but not daily
    ☐ on a daily basis Another useful measuring tool for wandering is the Woolsey Wandering Questionnaire (WWQ), presented below. A significant feature of the WWQ is that it also captures the burden of wandering behavior on the caregiver. This burden is assessed overall as a global impression and also with respect to each domain. It is administered weekly. Question 1 is a global impression of burden. Question 2 looks specifically at persistent or spontaneous wandering. Question 3 looks specifically elopement. Question 4 looks at pacing, a type of spontaneous walking that may be associated with agitation. Question 5 relates to spatial disorientation.

Each response can be assigned a numerical value, with more problematic behavior (first response) assigned the higher score. Thus, question 1 would be scored, for example, 4 for very problematic behavior and 1 for no wandering observed. Question 2 would be scored on a 5-point scale, with above average walking with no sitting being assigned a 5, and walking distinctly less than average being assigned a 1. In this way, each question can be assessed separately, or the tool may be assessed globally. The global assessment can be in terms of an overall score (all questions) or a burden score (only caregiver burden questions) or a wandering score (only the behavioral portions of questions 2-5).

| Woolsey Wandering Questionnaire |
| --- |

1. OVERALL, if wandering was observed, how problematic was the resident's wandering behavior this week?
    ☐ Very problematic
    ☐ Problematic
    ☐ Not problematic
    ☐ No wandering was observed
2. Relative to other residents of similar abilities this week, the subject (Purpose of question: assesses persistent wandering or wandering frequency)
    walked distinctly more than average and
        ☐ never sat
        ☐ rarely sat
        ☐ sat for periods
    did not walk distinctly more than average
        ☐ walked an average amount
        ☐ walked distinctly less than average
    2a) If resident walked more than average, how frequently?
    (Purpose of question: assess wandering frequency)
        ☐ On a daily basis
        ☐ Regularly but not daily
        ☐ On a few occasions
        ☐ N/A, resident did not walk more than average
    2b) How problematic was this behavior to you as a caregiver or staff?
        ☐ Very problematic
        ☐ Problematic
        ☐ Not problematic
3. How many times did the resident attempt to leave authorized areas or enter unauthorized areas? (Purpose of question: assesses elopement)
    ☐ More than twice (Estimated number of times: _____)
    ☐ Twice
    ☐ Once
    ☐ None
    3a.) How problematic was this behavior to you as a caregiver or staff?
        ☐ Very problematic
        ☐ Problematic
        ☐ Not problematic
4. Was the resident observed pacing, as evidenced by repetitively walking back and forth? (Purpose of question: pacing may suggest agitation)
    ☐ On a daily basis
    ☐ Regularly but not daily
    ☐ On a few occasions
    ☐ Not at all
    4a) How problematic was this behavior to you as a caregiver or staff?
        ☐ Very problematic
        ☐ Problematic
        ☐ Not problematic
5. Did the resident get lost? (Purpose of question: assesses wayfinding and/or spatial disorientation)
    ☐ On a daily basis
    ☐ Regularly but not daily
    ☐ On a few occasions
    ☐ Not at all
    5a) How problematic was this behavior to you as a caregiver or staff?
        ☐ Very problematic
        ☐ Problematic
        ☐ Not problematic In accordance with the treatment methods of the present invention, an effective amount of a ROCK inhibitor or a pharmaceutically acceptable salt thereof for administration one or more times a day may comprise from about 10 mg to about 1000 mg. Fasudil hydrochloride hemihydrate, for example, is suitably administered in a daily amount of about 10 mg to about 500 mg, about 10 mg to about 400 mg, about 10 mg to about 200 mg, about 10 mg to about 100 mg, about 20 mg to about 10 mg. One preferred dosing regimen involves the treatment with 20, 30 or 40 mg of Fasudil hydrochloride hemihydrate three times per day using an immediate-release formulation, for a total daily dose of 60-120 mg. Most preferred dosing exceeds a daily dose of 60 mg, with most preferred ranges for daily dosing being 70 mg to 120 mg administered in three equal amounts during the day. A particularly preferred daily dose is 90 mg per day. A further dosing regimen involves the treatment with, 30 to 60 mg of Fasudil hydrochloride hemihydrate only two times per day using an immediate-release formulation, for a total daily dose of 60-120 mg. A preferred embodiment is 45 mg of fasudil hydrochloride hemihydrate two times per day using an immediate-release formulation.

Certain patient sub-populations, such as renally impaired patients and/or older patients (e.g., 65 or older) may need lower doses or extended release formulations instead of immediate release formulations. Fasudil hydrochloride hemihydrate may have higher steady-state concentrations when given at usual doses to patients with renal disease and lower doses to lower the Cmax or delay the time to Cmax (increase the Tmax) may be required.

Kidney function is most often assessed using serum (and/or urine) creatinine. Creatinine is a breakdown product of creatine phosphate in muscle cells and it is produced at a constant rate. It is excreted by the kidneys unchanged, principally through glomerular filtration. Accordingly, elevated serum creatinine is a marker for kidney dysfunction and it is used to estimate glomerular filtration rate.

Normal levels of creatinine in the blood are approximately 0.6 to 1.2 mg/dL in adult males and 0.5 to 1.1 mg/dL in adult females. When creatinine levels exceed these figures, the subject has renal dysfunction, and is, therefore, treatable according to the invention. Mild renal impairment/dysfunction occurs in the range of 1.2 mg/dL to 1.5 mg/dL. Moderate renal impairment/dysfunction is considered to occur at creatinine levels exceeding 1.5 mg/dL. Severe renal impairment, which includes what is considered to be renal failure, is defined as a serum creatinine level of ≥2.0 mg/dL or the use of renal replacement therapy (such as dialysis). Treating subjects with mild, moderate and severe renal impairment is specifically contemplated.

As indicated, creatinine levels are considered to be a surrogate for glomerular filtration rate and serum creatinine levels alone may be used to estimate glomerular filtration rate using the Cockroft-Gault equation.

Generally, creatinine clearance of less than 60 mL/min (corresponding roughly to creatinine of >1.2 mg/dL) is considered moderate renal dysfunction. A glomerular filtration rate below 40 mL/min (corresponding approximately to creatinine levels exceeding 1.5 mg/dL) or especially 30 mL/min is considered severe renal dysfunction.

In general, creatinine clearance (estimated glomerular filtration rate) may be derived directly from serum creatinine using the Cockroft-Gault equation:

creatinine clearance=(((140−age in years)×(wt in kg))×1.23)/(serum creatinine in μmol/L)

For women the result of the calculation is multiplied by 0.85.

Empirically measured creatinine clearance may also be used directly as an estimate of glomerular filtration rate by looking at serum creatinine and urine creatinine levels. Specifically, urine is collected over 24 hours and the following equation is applied to ascertain creatinine clearance:

Creatinine Clearance (mL/min)=Urine Creatinine Concentration (mg/mL)*24 hour urine volume (mL)/Plasma Creatinine Concentration (mg/mL) *24 hour*60 minutes In one embodiment, dose of fasudil for mild to moderate renal impairment is reduced to 50-80 mg per day. In another embodiment, the dose of fasudil is not reduced but is administered one time per day in an extended release dosage form.

In another embodiment, the dose is not reduced for mild to moderate renal impairment.

In one embodiment, the dose of fasudil is reduced to 30-45 for severe renal impairment. In another embodiment, the dose of fasudil is not reduced but is instead administered one time per day in an extended release dosage form.

In a further embodiment, the dose is reduced where serum creatinine (SCr) >2 and/or an increase in SCr >1.5× from baseline, and/or a decrease in eGFR >25% from baseline.

Patient size is an important factor to consider when using creatinine-based estimates of renal function. The units of drug clearance are volume/time (mL/min), whereas the units of estimated GFR for chronic renal disease are volume/time/standard size (mL/min/1.73 m2). Generally doses may be adjusted down (e.g., 40-50 mg per day) for smaller patients and up for larger (e.g., 120 mg per day) for obese patients. A smaller male would be about 160 pounds or less. A smaller female patient would weigh about 130 pounds or less. Patients having a Body Mass Index of 30 and higher is considered obese.

In addition, older patients may need a lower dose at initiation, with a gradual increase to the recommended dose after days or weeks. In another embodiment, older patients may need lower doses for the duration of treatment. The aged population includes the "young old" who are 65-74, the "old old" who are 75-84 and the "frail elderly" who are 85 and older. For example, a starting dose of 30 mg per day for two weeks, followed by 60 mg per day for 4 weeks, then by 90 mg per day. Titration may even be warranted up to about 120 mg per day.

Another embodiment involves the treatment with 60-120 mg of Fasudil hydrochloride hemihydrate once per day in an extended release dosage form. Treatment with an extended release total daily dose of 90 mg Fasudil hydrochloride hemihydrate is preferred.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment.

Patients treatable according to the invention will typically score poorly on cognitive scales, such as the mini mental state exam (MMSE). A threshold of ≤23 on the MMSE is set for dementia, with score of ≤15 Representing severe dementia. Once the MMSE falls below 15, the Severe Impairment Battery (SIB) is a useful assessment too. Treatment using the inventive methods generally result in improved cognitive functioning. Patients will generally show improvement on the MMSE and the SIB of at least 3 points during the early stages of treatment and declines in cognition are slowed relative to control patients.

The MMSE, is described fully in Folstein (1975, 1987 and 2007). Generally, an MMSE score of 24-30 indicates no cognitive impairment, a score of 18-23 indicates mild cognitive impairment and 0-17 indicates severe cognitive impairment.

The methods of the invention also contemplate administering ROCK inhibitors with other compounds used to treat dementia or other symptoms of dementia. They may be administered in combination, a single dosage form, in a common dosing regimen or administered to the same patient at different times of the day using different dosing regiments.

In some embodiments, the patients are administered fasudil in combination with other actives approved to treat cortical dementia, including but not limited to cholinesterase inhibitors and NMDA receptor antagonists. In one embodiment, the cholinesterase inhibitor is selected from the group consisting of donepezil, rivastigmine, and galantamine. Exemplary doses of the cholinesterase inhibitors include 3-25 mg per day, more preferably 6-12 mg per day. In another embodiment, the NMDA receptor antagonist is memantine. In a specific embodiment, memantine is administered at a dose of 5-28 mg per day, preferably 15-20 mg per day. In a further embodiment, the co-administered active is a combination of donepezil and memantine at a dose of 28 mg memantine and 10 mg donepezil.

In a specific embodiment, the combination of fasudil with cholinesterase inhibitors is administered to wandering patients with proteinopathy-associated cortical dementia. In a further embodiment, the combination of fasudil with cholinesterase inhibitors is administered to wandering patients with mixed dementia, especially in patients who have progressive proteinopathy.

Dextromethorphan hydrobromide is another an uncompetitive NMDA receptor antagonist that also has activity as a sigma-1 receptor agonist. Marketed in combination quinidine sulfate (a CYP450 2D6 inhibitor), the product Nudexta is indicated for the treatment of pseudobulbar affect, which occurs in many forms of dementia.

In a specific embodiment, the patient is administered fasudil in combination with cholinesterase inhibitors or NMDA antagonists has Alzheimer's dementia.

In a specific embodiment, the patient is administered fasudil in combination with cholinesterase inhibitors has Lewy Body dementia In another embodiment, the patient is administered fasudil in combination with levodopa or a dopamine agonist, including but not limited to pramiprexole, ropinirole, apomorphine, and rotigotine. In a specific embodiment, the levodopa is administered in a dose of from about 30 to 2500 mg per day. In a further specific embodiment, the dopamine agonist is administered in a dose of from 0.25 to 10 mg per day. In another embodiment, fasudil is administered in combination with amantadine. In a specific embodiment, amantadine is administered in a dose of about 100-400 mg per day.

In yet another embodiment the patient is administered fasudil in combination with riluzole or edavarone at about 50 to 100 mg day.

In a further embodiment, the patient treated with fasudil is not also being treated with active agents including mood stabilizers, benzodiazepines, antipsychotics, anti-agitation drugs, or sleep aids. In a specific embodiment, the patient treated with fasudil is not being treated with risperidone, ariprprazole, quetiapine, carbamazepine, gabapentin, prazocin, trazodone or lorazepam.

In a further embodiment the patient treated with fasudil is being treated for depression. In a specific embodiment, the patient is treated with an anti-depressant such as citalopram or escitalopram.

Example 1

A clinical trial is conducted in order to determine the effectiveness of oral fasudil in reducing the frequency of wandering in patients with Alzheimer's Dementia (AD) and frontotemporal dementia (FTD).

Twenty patients, 10 with AD and 10 with FTD and an MMSE score ≤23, who are characterized wanderers, are enrolled into the study and observed for 2 weeks to confirm wandering behavior. Confirmed wanderers receive fasudil in an open-label run in period for 6 weeks at 90 mg/day (30 mg TID) to evaluate any effect on wandering and then enter the double-blind phase where they receive test drug 90 mg/day (30 mg TID) or matching placebo (TID) for 6 weeks. The double-blind phase is followed by another treatment period of 6 weeks with the opposite treatment assignment (placebo or test drug taken with food).

The following inclusion criteria are applied:
1. Patients 50 years to 90 years of age.
2. Diagnosis of dementia (AD or VaD or mixed type) for at least 6 months.
3. For entering observation period and for entering open label treatment period: Wanders:
   a. Walks distinctly more than average as others of same age and ability AND/OR
   b. Elopement behavior ≥3×per week in the opinion of the investigator For entering first double-blind treatment period:
Wanders:
   a. Walks less than half the mean distance measured in observation period AND/OR
   b. Elopement behavior <1× per week in the opinion of the investigator AND/OR
   c. Wandering has improved in the opinion of the Investigator.
4. For entering observation period and for entering open label treatment period:
   a. MMSE between 10 and 25.

Wandering is measured in term of time in motion and distance traveled (measures of persistent wandering), attempted and successful boundary transgressions (measures of elopement) and patterns like pacing a lapping (indicative of persistent wandering and/or agitation or anxiety) using an electronic tracking device. A typical tracking device would use a combination of accelerometry with positioning, using technology like RFID or Bluetooth in an indoor environment and GPS outdoors. Other wayfinding, orientation and memory-associated wandering incidents are observed and recorded manually.

Wandering is measured in term of time in motion and attempted successful boundary transgression using an electronic tracking device. Other wayfinding, orientation and memory-associated wandering incidents are observed and recorded manually.

The Mini Mental State Exam (MMSE), Woolsey Wandering Questionnaire and Revised Algase Wandering Scale are administered at baseline and at the end of each treatment period. Any change in the use of antipsychotics or anxiolytics that could affect movement during the study is strongly discouraged.

Treatment with fasudil is associated with a significant reduction in wandering. Persistent wanderers reduce activity levels by about 50% while on drug as compared to placebo and this is accompanied by a mean increase in MMSE score of greater than 3 points. Sporadic wanderers show a significant reduction in wayfinding errors and other problematic behaviors while on drug, with a similar improvement in MMSE.

LIST OF REFERENCES

Algase D L, Beattie E R, Bogue E L, Yao L. 2001a. The Algase Wandering Scale: initial psychometrics of a new caregiver reporting tool. Am J Alzheimers Dis Other Demen. 16:141-152.

Algase D L, Beattie E R, Therrien B. 200 1b. Impact of cognitive impairment on wandering behavior. West J Nurs Res. 23:283-95.

Aud M A. Dangerous wandering: elopements of older adults with dementia from long-term care facilities. Am J Alzheimers Dis Other Demen. 2004; 19(6):361-368.

Ballard C G, Mohan R N C, Bannister C, Handy S, Patel A. 1991. Wandering in Dementia Sufferers. Int J Geriatr Psych 6:611-614.

Bathgate D, Snowden J S, Varma A, et al. 2001. Behaviour in frontotemporal dementia, Alzheimer's disease and vascular dementia. Acta Neurol Scand. 103:367-378.

Ceyzériat K, et al., Learning from the Past: A Review of Clinical Trials Targeting Amyloid, Tau and Neuroinflammation in Alzheimer's Disease. Current Alzheimer Research. 2020; 17: 1-13.

Chen M, Liu A, Ouyang Y, Huang Y, Chao X, Pi R. 2013. Fasudil and its analogs: a new powerful weapon in the long war against central nervous system disorders? Expert Opin Investig Drugs. 22:537-50.

Cipriani G, Lucetti C, Nuti A, Danti S. 2014. Wandering and dementia. Psychogeriatrics. 14:135-42.

Cooper J K, Mungas D. 1993. Risk factor and behavioral differences between vascular and Alzheimer's dementias: the pathway to end-stage disease. J Geriatr Psychiatry Neurol. 6:29-33.

Couch B A, DeMarco G J, Gourley S L, Koleske A J, Increased Dendrite Branching in AβPP/PS1 Mice and Elongation of Dendrite Arbors by Fasudil Administration. Alzheimers Dis. 2010; 20(4): 1003-1008.

Elliott C, Rojo A, Ribe E, Broastock M, Xia W, Morin P, Semenov M, Baillie G, Cuadrado A, Al-Shawi R, Ballard C, Simons P, Killick R, A role for APP in Wnt signalling links synapse loss with β-amyloid production. Translational Psychiatry. 2018; 8(179).

Erkinjuntti T, Inzitari D, Pantoni L, Wallin A, Scheltens P, Rockwood K, Desmond D W. 2000. Limitations of clinical criteria for the diagnosis of vascular dementia in clinical trials. Is a focus on subcortical vascular dementia a solution? Ann N Y Acad Sci. 903:262-72.

Feng Y, LoGrasso P, Defert O, Li R, Rho Kinase (ROCK) Inhibitors and Their Therapeutic Potential. J Med Chem. 2016; 59*6): 2269-2300.

Folstein M F, Folstein S E, McHugh P R. "Mini-mental state": a practical method for grading the cognitive state of patients for the clinician. J Psychiatr Res. 1975; 12:189-198.

Hamano T, Shirafuji N; Yen S; Yoshida H, Kanaan N, Hayashi K, Ikawa M, Yamamura O, Fujita Y; Kuriyama M, Nakamoto Y, Rho-kinase ROCK inhibitors reduce oligomeric tau protein. Neurobiology of Aging; 2020; 89: 41-54.

Hou Y, Zhou L, Yang Q D, Du X P, Li M, Yuan M, Zhou Z W, Changes in hippocampal synapses and learning memory abilities in a streptozotocin-treated rat model and intervention by using fasudil hydrochloride. Neuroscience. 2012; 200: 120-129.

Human Rights Watch. 2018. They Want Docile: How Nursing Homes in the United States Overmedicate People with Dementia. ISBN: 978-1-623-135720. Downloaded 17 May 2019 from www.hrw.org.

Jacobs M, Hayakawa K, Swenson L, Bellon S, Fleming M, Taslimi P, Doran J, The structure of dimeric ROCK I reveals the mechanism for ligand selectivity. J Biol Chem. 2006; 281(1): 260-68.

Kamei S, Oishi M, Takasu T. 1996a. Evaluation of fasudil hydrochloride treatment for wandering symptoms in cerebrovascular dementia with 31P-magnetic resonance spectroscopy and Xe-computed tomography. Clin Neuropharmacol. 19:428-38.

Kamei S, Toshiaki T, Oishi M, Effect of fasudil hydrochloride on wandering symptoms of c cerebrovascular dementia patients. Neurotherapy. 1996b 13:43-50.

Kim K W, Lee D Y, Jhoo J H, Youn J C, Suh Y J, Jun Y H, Seo E H, Woo J I, Diagnost accuracy of mini-mental status examination and revised Hasegawa dementia scale for Alzheimer's disease. Dement Geriatr Cogn Disord. 2005; 19(5-6):324-30.

Klein D A, Steinberg M, Galik E, Steele C, Sheppard J M, Warren A, Rosenblatt A, Lyketsos C, Wandering behaviour in community-residing persons with dementia. Intl J Geriatric Psychiatry. 1999. 14(4): 272-279.

Knuffman J, Mohsin F, Feder J, Grossberg G T. 2001. Differentiating between lewy body dementia and Alzheimer's disease: a retrospective brain bank study. J Am Med Dir Assoc. 2:146-8.

Lai C K, Arthur D G. Wandering behaviour in people with dementia. J Adv Nurs. 2003; 44(2):173-182.

Logsdon R, Teri L, Mccurry S, Gibbons L E, Kukull W A, Larson E B, Wandering: A Significant Problem among Community Residing Individuals with Alzheimer's Disease. The Journals of Gerontology Series B Psychological Sciences and Social Sciences. 1998; 53(5):P294-9.

Nakagawa O, Fukisawa K, Ishizaki T, Saito Y, Nakao K, Narumiya S, ROCK-I and ROCK-II, two isoforms of Rho-associated coiled-coil forming protein serine/threonine kinase in mice. FEBS Lett. 1996 Aug. 26; 392(2): 189-93.

Nakaoka A, Suto S, Makimoto K, Yamakawa M, Shigenobu K, Tabushi K. 2010. Pacing and lapping movements among institutionalized patients with dementia. Am J Alzheimers Dis Other Demen. 25:167-72.

Nelson & Algase (Eds) Evidence-based Protocols for Wandering Behaviour (2006), Springer: NY. Risk Model.

Roman G C, Tatemichi T K, Erkinjuntti T, Cummings J L, Masdeu J C, Garcia J H, Amaducci L, Orgogozo J M, Brun A, Hofman A, et al. 1993. Vascular dementia: diagnostic criteria for research studies. Report of the NINDS-AIREN International Workshop. Neurology. 43:250-60.

Roman G C. 2004. Facts, myths, and controversies in vascular dementia. J Neurol Sci. 226:49-52.

Rovner B W, Folstein M F. Mini-mental state exam in clinical practice. Hosp Pract. 1987; 22(1A):99, 103, 106, 110.

Salardini A. 2019. An Overview of Primary Dementias as Clinicopathological Entities. Semin Neurol. 39:153-166.

Sasaguri H, Nilsson P, Hashimoto S, Nagata K, Saito T, De Strooper B, Hardy J, Vassar R, Winblad B, Saido T C, APP mouse models for Alzheimer's disease preclinical studies. EMBO J. 2017; 36(17): 2473-2487.

Sellers K, Elliott C, Jackson J, Ghosh A, Ribe E, Rojo A, Jarosz-Griffiths H H, Watson A A, Xia W, Semenov M, Morin P, Hooper N, Porter R, Preston J, Al-Shawi R, Baillie G, Lovestone S Cuadrado A, Harate M, Simons P, Srivastava D P, Killick R, Amyloid B synaptotoxicity is Wnt-PCP dependent and blocked by fasudil. Alzheimer's & Dementia. 2018; 14: 306-317.

Shibuya M, Asano T, Sasaki Y. 2001. Effect of Fasudil HCl, a protein kinase inhibitor, on cerebral vasospasm. Acta Neurochir Suppl. 77:201-4.

Turk M. The Effect of Rho Kinase Inhibitors on Alzheimer's Disease, Dissertation. Arizona State University. May 2017.

Uehata M, Ishizaki T, Satoh H, Ono T, Kawahara T, Morishita T, Tamakawa H, Yamagami K, Maekawa M, Narumiya S, Calcium sensitization of smooth muscle mediated by a Rho-associated protein kinase in hypertension. Nature. 1997 Oct. 30; 389(6654):990-4.

US Census: www.census.gov

Wick J Y and Zanni G R, Aimless Excursions: Wandering in the Elderly, The Consultant Pharmacist. 2006; 21(8): 608-18.

Yamaguchi H, Miwa Y, Kasa M, Kitano K, Amano M, Kaibuchi K, Hakoshima T, Structural basis for induced-fit binding of Rho-kinase to the inhibitor Y-27632. J Biochem. 2006 September; 140(3):305-11.

Yayama S, Yamakawa M, Suto S, Greiner C, Shigenobu K, Makimoto K. 2013. Discrepancy between subjective and objective assessments of wandering behaviours in dementia as measured by the Algase Wandering Scale and the Integrated Circuit tag monitoring system. Psychogeriatrics. 13:80-7.

Yu J, Gu Q, Yan Y, Yu H, Guo M, Liu C, Song G, Chai Z, Wang Q, Zia B, Zhang H, Jiang Y, Cungen M A, Fausidil improves cognition of APP/PS1 transgenic mice via inhibiting the activation of microglia and shifting microglia phenotypes from M1 to M2. Chin J Cell Mol Immunol. 2017; 33(12): 1585-1593.

The disclosure of each reference set forth herein is incorporated herein by reference in its entirety.

The invention claimed is:

1. A method of treating wandering in a patient with dementia with Lewy bodies (DLB), comprising administering a therapeutically effective amount of a fasudil to said patient.

2. The method according to claim 1 wherein the patient does not have vascular dementia.

3. The method according to claim 1 wherein the patient suffers from persistent wandering.

4. The method according to claim 1 wherein the patient moves at least 20% of their waking time.

5. The method according to claim 1 wherein the patient does not exhibit problems with wayfinding.

6. The method according to claim 1 wherein the treatment results in a greater-than 3-point improvement on the mini mental state exam.

7. The method according to claim 2, wherein the treatment results in at least a 50% reduction in the time the patient is in motion.

8. The method according to claim 1 where said treatment continues for at least 6 months.

9. The method according to claim 7, wherein fasudil is administered in a dose exceeding 60 mg per day.

10. The method according to claim 6, wherein fasudil is administered in three equal portions throughout the day.

11. The method according to claim 1, wherein fasudil is administered in a total daily dose of between 70 mg and 120 mg.

12. The method according to claim 1, wherein fasudil is administered at a total daily dose exceeding 70 mg and is administered in a sustained release formulation.

* * * * *

UNITED STATES PATENT AND TRADEMARK OFFICE
CERTIFICATE OF CORRECTION

| | |
|---|---|
| PATENT NO. | : 11,642,352 B2 |
| APPLICATION NO. | : 17/144802 |
| DATED | : May 9, 2023 |
| INVENTOR(S) | : Thomas MacAllister |

It is certified that error appears in the above-identified patent and that said Letters Patent is hereby corrected as shown below:

On the Title Page

Item (54) and in the Specification, Column 1, Lines 1-2, Please adjust the title of the invention as follows:
METHODS OF TREATING WANDERING IN LEWY BODY DEMENTIA Signed and Sealed this
First Day of August, 2023

*Katherine Kelly Vidal*

Katherine Kelly Vidal
*Director of the United States Patent and Trademark Office*